United States Patent [19]
Clark et al.

[11] Patent Number: 4,723,948
[45] Date of Patent: Feb. 9, 1988

[54] CATHETER ATTACHMENT SYSTEM

[75] Inventors: Richard J. Clark, Norfolk; Gary R. Whipple, South Attleboro, both of Mass.

[73] Assignee: Pharmacia Nu Tech, Walpole, Mass.

[21] Appl. No.: 930,135

[22] Filed: Nov. 12, 1986

[51] Int. Cl.$^4$ .......................................... A61M 25/00
[52] U.S. Cl. ................................... 604/283; 604/103; 604/905; 285/243
[58] Field of Search ............... 604/283, 103, 905, 165; 285/315, 243, 255

[56] References Cited

U.S. PATENT DOCUMENTS

| | | | |
|---|---|---|---|
| 3,073,628 | 1/1963 | Cline et al. | 285/243 |
| 3,087,746 | 4/1963 | Hamilton | 285/243 |
| 4,402,691 | 9/1983 | Rosenthal et al. | 604/905 X |
| 4,473,369 | 9/1984 | Lueders et al. | 604/283 X |
| 4,631,056 | 12/1986 | Dye | 604/905 |

*Primary Examiner*—Stephen C. Pellegrino
*Attorney, Agent, or Firm*—Cesari and McKenna

[57] ABSTRACT

This connection system has particular application to releasably securing a flexible catheter to a rigid portal outlet stem received in the catheter lumen. The system includes a radial enlargement on the outlet stem and a retainer sleeve having a tubular distal segment which encircles the catheter at a location adjacent to the free end of the stem therein and a proximal segment which is composed of a pair of mirror image, hinged together, semicylindrical clamping sections, one of which is an integral extension of the distal sleeve segment and the other of which can be moved between open and closed positions so as to enable the sections to clamp around the stem enlargement and a segment of the catheter encircling the stem. A locking ring snugly encircles the sleeve and is slidable therealong between a locking position wherein it tightly engages around the sleeve clamping sections and an unlocking position wherein it encircles the distal sleeve segment. The system assures a secure, fluid-tight connection of the catheter to the stem and provides strain relief for the catheter.

20 Claims, 4 Drawing Figures

CATHETER ATTACHMENT SYSTEM

This invention relates to a catheter. It relates more particularly to improved means for connecting a flexible infusion catheter to a source of infusate.

BACKGROUND OF THE INVENTION

The treatment of certain diseases of the human body often requires the short-term or long-term infusion of drugs, blood products or nutritional or other fluids into the patient's venous or arterial system. While such fluids can be administered extracorporeally by transcutaneous injection, in some cases, as when a particular patient's regime requires repeated access for drug infusion, or where infection is of acute concern, it is desirable to provide the patient with a totally implanted infusion system.

Such a system includes an injection portal which is an infusate chamber implanted subcutaneously and placed on the chest wall or other convenient body location. The portal is fitted with a needle-penetrable septum which is located directly under the skin by which drugs or other fluids may be introduced into the portal by transcutaneous injection through the septum. The portal has a fluid outlet tube or stem which is connected to one end of a flexible catheter which leads to the infusion site which is usually a blood vessel or particular body cavity, e.g., the peritoneum. Since the system is completely implanted, it reduces the risk of infectious complications and allows drug infusion which is targeted to the specific patient malady. Even though the delivery system may be implanted for a long period, the patient remains ambulatory and can be treated on an out-patient basis and the system does not interfere with the normal daily activities of the patient.

A similar prosthesis can be used to draw blood from an artery or vein for blood sampling purposes.

Since an implantable device of this type may remain in the patient's body for many months, it is essential that the connection of the catheter to the portal remain secure and fluid-tight during the entire period of implantation. If the connection should fail or if there should be an infusate leak at that location, the infusate dose required to treat the patient which is injected into the portal will not be conducted to the targeted infusion site in the patient's body. Rather, some or all of the infusate will be dispensed at the site of the portal and could cause complications at that body location. In this connection, it should be appreciated that after a drug delivery system is implanted, the catheter is subjected to various stresses and strains due to movements of the patient's body, weight changes, etc. These are reflected in tensile and twisting forces at the connection of the catheter to the portal outlet which tend to upset the integrity of that union.

In an attempt to avoid this leakage problem and the attendant complications, various steps have been taken to strengthen the connection between the catheter and the portal. These include the providing of raised circular rings or ribs on the portal outlet stem over which the catheter wall is stretched. These lines of localized resilient engagement resist sliding movements of the catheter from the portal stem. In some systems, the connection is made somewhat more secure by providing a locking ring or bushing which encircles the catheter and is releasably captured on the catheter segment engaged on the portal stem by the raised ribs thereon.

We have found, however, that these prior catheter connections are not entirely satisfactory. Sometimes the tensile forces exerted on the catheter due to movements of the patient still suffice to separate the catheter from the portal or to tear the catheter at that point of connection because of a poor distribution of stresses on the catheter wall. Certain prior systems are disadvantaged in that it is quite difficult to connect the catheter to the portal outlet stem. This is because that stem is often very small (e.g. 1 mm OD), and to make the connection, the stem must be threaded into the end of the catheter lumen which is itself equally small. Furthermore, when inserting the portal stem into the catheter, if one is not quite careful, the catheter will be punctured by the end of stem which, being so small, constitutes a sharp point.

In addition, it should be kept in mind that it may be necessary to disconnect the catheter from an already implanted injection portal in the event that the catheter has to be replaced for one reason or another. For example, it sometimes happens that the catheter lumen becomes clogged by clots or other debris. Therefore, it is desirable that any connection between the catheter and the portal be separable from the portal with a minimum amount of effort and finger manipulation by the surgeon who must make that repair subcutaneously. The prior catheter connection systems of which applicant is aware, do not facilitate such ready connection and disconnection of the catheter to and from the portal.

SUMMARY OF THE INVENTION

Accordingly, the present invention aims to provide an improved catheter connection system.

Another object of the invention is to provide a catheter connection system which is very strong, yet which can be released quite easily if the need should arise.

Another object of the invention is to provide a catheter connection which is specially adapted for use in an implantable infusion system for joining the catheter to an injection portal.

Yet another object of the invention is to provide a connection system of this type which minimizes localized stresses on the catheter in the region of the connection.

Other objects will, in part, be obvious and will, in part, appear hereinafter.

The invention accordingly comprises the features of construction, combination of elements and arrangement of parts which will be exemplified in the following detailed description, the scope of the invention will be indicated in the claims.

The catheter connection system of interest here may be used in any application where it is necessary to releasably connect the end of a flexible resilient catheter or other tube to a stem, tube or rod by inserting the stem, tube or rod into the end of the catheter. Since the invention has particular application to the connection of a catheter to the outlet stem of an implantable injection portal, we will describe the invention in this context. It should be understood, however, that the invention may be applied to other applications where similar flexible tube-to-rigid-tube connections are required.

Briefly, the present connection system involves the coaction and cooperation of a flexible resilient catheter, a relatively rigid stem or tube onto which the catheter is slid to effect the connection and a specially designed, clam shell-type locking retainer which encircles the stem and catheter segment thereon to retain the catheter on the stem. The system provides strain relief to the catheter and minimizes localized stresses on the catheter due to tensile and other forces exerted on the catheter in use.

The stem component of the system is formed with an axially symmetric radial enlargement. In one arrangement, this projection takes the form of a three-dimensional barb or bulb whose pointed end corresponds to the distal end of the stem. This barb, rather than being pointed with sharp edges, is generally pear-shaped with a blunted distal end whose diameter is less than the diameter of the lumen in the catheter being connected to the stem and a larger proximal end that is appreciably larger than that lumen.

When sliding the catheter onto the end of the stem, the barb end functions as a guide to center the stem in the catheter lumen to facilitate sliding the catheter onto the stem, the elastic wall of the catheter stretching outward as required to accommodate the larger diameter proximal end of the barb. Thus, when the end segment of the catheter has received the full extent of the stem, the catheter resiliently engages the outer surface of the stem and conforms closely to the barbed segment thereof.

In another embodiment of my system, the stem enlargement is located at the proximal end of the stem and is not encircled by the catheter segment slid onto the stem.

The third component of my connection system, namely the retainer, includes a sleeve which is engaged on and encircles the catheter prior to sliding the end of the catheter onto the portal stem. The sleeve has a distal end segment which is tubular and faces the distal end of the catheter, i.e., the end thereof not being connected to the portal. The opposite or proximal end segment of the sleeve is split lengthwise into two mirror-image, hinged together sections that form a clamshell arrangement. That is, one half of this split sleeve segment is a collinear extension of the tubular sleeve segment and the other half is hinged to the first half so that it can be swung open and closed; when closed, those split segments form a tubular extension of the tubular sleeve segment.

The passage through the tubular segment of the sleeve is sized to snugly receive the catheter so that when the split segment of the sleeve is open, the sleeve can be slid along the catheter so that it encircles the length thereof that surrounds the outlet stem of the injection portal. The passage through the split segment of the sleeve includes a radial enlargement extending around both halves of that segment and which corresponds in size and location to the radial enlargement or barb on the portal stem. When the sleeve is slid onto the catheter segment surrounding the portal stem and the movable or swingable half of the split sleeve segment swung to its closed position, that sleeve segment encircles and captures the stem enlargement and any catheter wall segment stretched around that enlargement.

The retainer also includes a locking ring which reposes on the tubular segment of the sleeve when the split segment thereof is open. After the hinged half of the split sleeve segment is swung closed to clamp the stem enlargement, that ring may be slid along the sleeve so that it tightly encircles the split sleeve segment to maintain that segment in its closed, clamping condition.

As will be described shortly in greater detail, when the retainer component of my connection system is seated on the portal stem and catheter thereon and locked in place, there results a very secure connection of the catheter to the stem. Even very strong pulling, twisting and bending forces exerted on the catheter are unable to disconnect the catheter from the outlet tube or to break the fluid-tight integrity of that connection. Actually, as will be seen, such forces enhance that connection. Moreover, those forces are distributed over a relatively wide area of the catheter wall to minimize the build-up of localized strains in the catheter wall which could result in a puncture or tear in that wall. As a result, even when very large tensile forces are applied to the catheter, the catheter will usually break somewhere along its length before its connection to the portal outlet stem will fail.

The catheter connection system described here is also quite easy and inexpensive to make, being composed of simple, molded plastic and metal parts which can be manufactured in quantity at minimum cost. Also, the connection is easy to make and to release, even if that needs to be done in the case of an injection portal already implanted in the body. In other words, the present apparatus facilitates sliding a catheter onto the end of a portal outlet stem and simple finger movements suffice to manipulate the connector's retaining sleeve and locking ring to secure the catheter to the stem or to release the catheter from the stem. Consequently, the present connection system should find wide application wherever it is necessary to releasably connect a flexible catheter or other tube to a relatively rigid rod or stem.

BRIEF DESCRIPTION OF THE DRAWING

For a fuller understanding of the nature and objects of the invention, reference should be had to the following detailed description taken in connection with the accompanying drawing, in which.

DETAILED DESCRIPTION OF THE PREFERRED EMBODIMENTS

Figure 1:
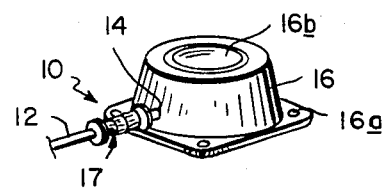
FIG. 1 is a fragmentary isometric view of an implantable infusion portal incorporating a catheter connection system of this invention.

Referring to FIG. 1 of the drawing, my catheter connection system indicated generally at 10 is shown connecting the proximal end of a catheter 12 to the tubular outlet stem 14 of an implantable injection portal 16. The portal is made of a material, such as stainless steel, and in use it is implanted at a convenient location in the body, such as on the chest wall. This portal might be used, for example, to conduct infusate to a vein leading from the heart. Usually, small eyes 16a are provided around the base of the portal through which sutures may be passed to anchor the portal to the chest wall. The portal also includes a septum 16b composed of a suitable resilient, needle-penetrable material, such as silicone rubber. When the portal is implanted, the septum is situated directly under the patient's skin so that infusate can be introduced into the portal by transcutaneous injection through septum. The infusate thereupon flows through the portal outlet stem 14 to the catheter 12 whose distal end is placed at a selected infusion site in the body, such as a blood vessel or a body cavity such as the peritoneum. Catheter 12 is made of a flexible, resilient biocompatible material, such as silicone rubber.

The inside diameter of the catheter, which corresponds more or less to the outside diameter of portal stem 14, may vary depending upon the particular application, from, say, 0.5 to 3.0 mm. Likewise, the volume of the portal 16 may vary from, say, 0.4 ml to 1.0 ml.

Figure 2:
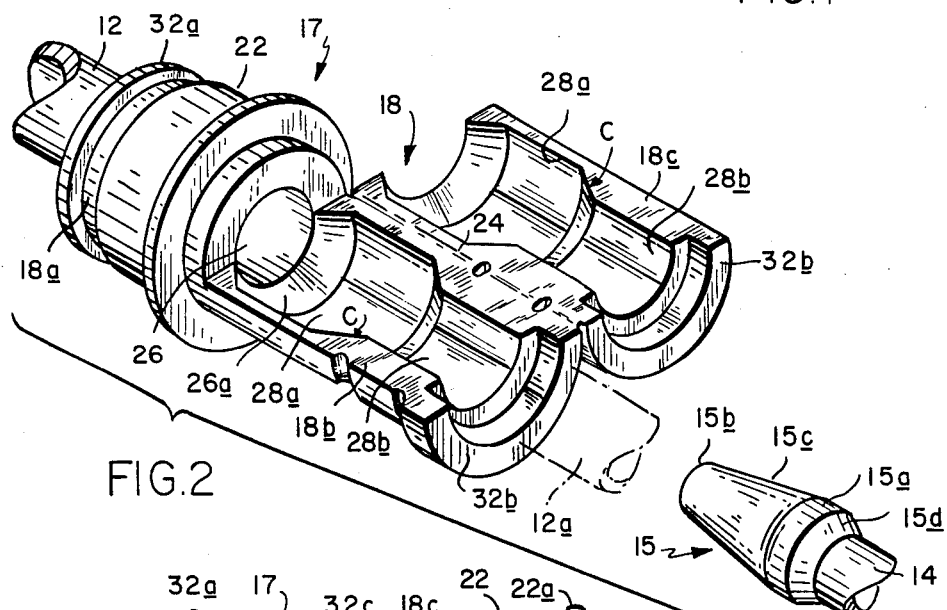
FIG. 2 is a fragmentary, exploded, isometric view on a much larger scale showing the catheter connection system in greater detail.

Referring now to FIG. 2 of the drawing, connection system 10 is composed of three distinct parts or components. These include the proximal end segment 12a of the catheter, the portal outlet stem 14 and a special locking retainer shown generally at 17. The tubular stem 14 is formed with a radial enlargement 15 along its length. In the system embodiment depicted in FIG. 2, the enlargement 15 is located at the outer or distal end of the stem and it takes the form a pear-shaped bulb or barb. In other words, the enlargement has a relatively large, rounded shoulder 15' whose diameter is appreciably larger than the inside diameter of catheter 12. The enlargement tapers from that shoulder to a relatively small diameter blunt end 15b whose diameter is appreciably smaller than the inside diameter of the catheter. Accordingly, it is relatively easy to align the proximal end of the catheter with the enlargement end 15b to engage the catheter on the stem 14.

The shape of the enlargement is such that a relatively long frustoconical segment 15c of the enlargement can be introduced into the catheter lumen for a distance corresponding to about half its length without extending or stretching the catheter wall. Further penetration of the outlet tube into the catheter segment 12a results in the catheter wall deforming to accommodate enlargement 15, particularly shoulder 15a. That is, the silicone plastic catheter 12 is a very visco-elastic material that flows when put under compression. This property is used to apply ever-increasing force on the catheter to effect its sliding connection to stem 14. Thus, as shown in FIG. 3, due to the resiliency of the catheter material, the catheter segment 12a assumes the shape of outlet stem 14, including enlargement 15.

Figure 3:
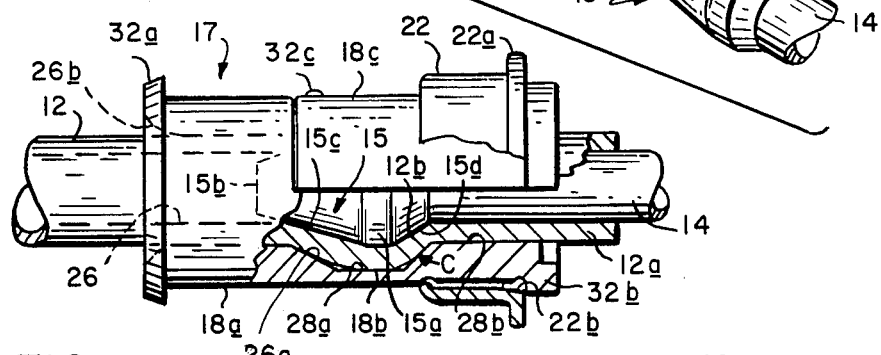
FIG. 3 is a side elevational view with parts in section of the connection system.

Referring now to FIGS. 2 and 3, the locking retainer 17 comprises two distinct parts, namely a tubular retainer sleeve indicated generally at 18 and a locking ring 22 slidably engaged around sleeve 18. Desirably, sleeve 18 is a molded part made of a suitable biocompatible plastic material, such as polypropylene. Ring 22 is likewise an easily fabricated, relatively inexpensive stamped metal (e.g., stainless steel) or molded plastic (e.g., polypropylene) part.

Retainer sleeve 18 is a unitary piece that has three sections. It has a tubular section 18a at the distal end of the sleeve which encirles the catheter. Projecting forwardly from section 18a, i.e., toward the portal 16, is a semi-cylindrical section 18b which is collinear with section 18a. In other words those two sections have a common longitudinal axis of curvature. The third sleeve section 18c is likewise a semi-cylinder and it is connected edgewise by means of a living hinge 24 to an edge of section 18b so that section 18c can be swung between an open position shown in FIG. 2 and a closed position illustrated in FIG. 3. In other words, sleeve sections 18b and 18c constitute a clamshell arrangement which projects from the proximal end of sleeve section 18a so that when section 18c is in its closed position, the sleeve 18 as a whole constitutes a continuous tube whose outer diameter is more or less the same along the length of the sleeve.

As best seen in FIG. 2, the sleeve section 18a has an axial passage 26 whose diameter is more or less the same as the outer diameter of catheter 12 so that the catheter is snugly received in that passage. As noted previously, the inner diameter of the unstressed catheter 12 corresponds to the diameter of enlargement 15 partway along the length of that enlargement. Thus, when the catheter segment 12a is engaged on portal stem 14, sleeve 18 can be slid toward the proximal end of the stem until enlargement 15 projects partway into the end of passage 26 of sleeve section 18a, as shown in dotted lines in FIG. 3. Preferably, the proximal end of that passage is tapered at 26a to more or less match the taper of stem enlargement 15 as shown in FIG. 2. As seen there, this locates the enlargement shoulder 15a positioned opposite sleeve section 18b. The opposite or distal end 26b of passage 26 is flared as shown in FIG. 3., for reasons to be described later.

Still referring to FIG. 2, the inside wall of section 18b has a semicylindrical recess 28a at the distal end of that section which is sized to receive enlargement shoulder 15a, including the catheter segment stretched thereon. The remaining length 28b of that interior wall has more or less the same diameter as passage 26 in sleeve section 18a. Accordingly when sleeve section 18c is in its open position shown in FIG. 2, and the sleeve is slid along the stem 14 until it is stopped by the engagement of enlargement 15 with the wall of passage 26, the catheter segment 12a and stem 14 will lie coaxially in sleeve section 28a, with the enlargement shoulder 15a being seated in recess 28a in that section.

Sleeve section 18c is a mirror image of section 18b so that it has a semicylindrical recess 28a and wall segment 28b that match those in section 18b. Thus, when section 18c is swung to its closed position shown in FIG. 3, catheter segment 12a and portal stem 14, including its enlargement 15, are captured between the two sleeve sections 18b and 18c as clearly seen in that drawing figure.

With these two sections closed together as shown, the locking ring 22 can be slid from sleeve section 18a along the sleeve so as to encircle and capture sleeve sections 18b and 18c, thereby maintaining sections 18c in its closed position. The inside diameter of the ring is held in close tolerance to the outside diameter of the sleeve to maintain position and closing pressure on sleeve section 18c and, thus, clamping force on catheter 12. Desirably, that ring has a flange 22a to strengthen the ring and to provide a gripping location for the surgeon. Also, as shown in FIG. 3, it may have a lead angle or bevel 22b on its inside wall to facilitate its sliding onto sleeve sections 18b and 18c. Radial flanges 32a and 32b are formed at the opposite ends of sleeve 18 in order to limit the sliding motion of ring 22. Preferably also, sleeve 18 has an interference diameter bump, rib, or other enlargement 32c on its outer wall adjacent to the distal ends of sections 18b and 18c thereof to inhibit ring 22 from sliding from its locking position shown in FIG. 3 to its unlocking position illustrated in FIG. 2. In other words, an appreciable axial force should be required to slide the ring 22 from sections 18b to its unlocking position on section 18a.

It will be appreciated from the foregoing that the connection of catheter 12 to outlet stem 14 can be made quite easily with one hand, even when the surgeon has no clear view of the connection site. To do this, the surgeon grasps the end of the catheter and, feeling with his fingers, slides the catheter onto the pointed end 15b of portal stem 14. He then pushes the end of the catheter over enlargement 15 until the catheter engages portal 16. Next, the surgeon slides retainer sleeve 18 along the catheter until that sliding motion is stopped by the engagement of the sleeve passage 26 wall by the portion of catheter 12 that is stretched by stem enlargement 15 to a diameter greater than the diameter of passage 26. Then the surgeon swings sleeve section 18c to its closed position and slides the locking ring 22 to its stop at sleeve flange 32b. Removal of the catheter 12 from stem 14 simply involves reversing the above procedure.

When the connection 10 is made and locked as shown in FIG. 3, it is practically impossible to pull catheter 12 from the portal stem 14. The aforementioned flare 26b at the distal end of sleve passage 26 provides strain relief to the catheter to prevent its being damaged when the catheter is tensioned at an angle to the sleeve centerline or axis. Any pulling or twisting forces applied to the catheter only serve to tighten the connection between the catheter and the outlet stem. That is, when catheter 12 is tensioned, it stretches so that its wall becomes thinner as it moves axially. Sleeve 18, being in contact with the catheter is pulled with the catheter. Resultantly, a circular area of contact C (FIGS. 2 and 3) of the passage 26 wall is moved closer to a short frustoconical surface 15d of barb 15 located proximate to the inner end of the stem 14, thereby increasing the clamping force on the catheter. Thus, such tensile loads effectively pull enlargement 15 even more tightly into the sleeve section passage 28b. Accordingly, a frustoconical catheter segment 12b is sandwiched or compressed ever more tightly between enlargement 15 and the end of passage 28b, as clearly seen in FIG. 3. That engaged segment 12b of the catheter is centered in passage 28b and the areal contact is sufficiently small to cause considerable compression or "squeeze" on the catheter, but not so small as to produce localized stresses on the catheter wall that might tend to cause tears or punctures in that wall. Consequently, there is very little likelihood of the catheter pulling away from the portal outlet stem 14 or tearing due to movements of the patient in which the prosthesis is implanted so that the integrity of the connection system 10 should be maintained for the entire period of implantation. Yet, if it should become necessary to replace the catheter 12 for some reason, the present system 10 facilitates that as well. Indeed, the same locking retainer and portal stem can be assembled and disassembled many times if need be.

Figure 4:
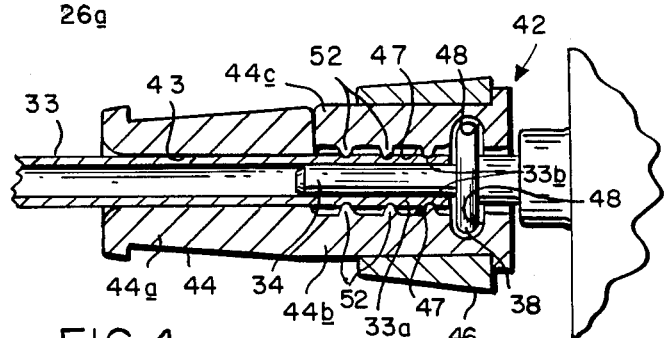
FIG. 4 is a similar view of another embodiment of the catheter connection system.

FIG. 4 illustrates another connection system embodiment. This arrangement is particularly useful for connecting to a portal stem or tube 34 a catheter 33, made of a material such as polyurethane which is quite strong and can withstand compression without cutting, tearing or thinning. In this arrangement, the stem 34 has an enlargement consisting of a single radial flange 38, located adjacent the proximal end of the stem. In use, the end segment 33a of the catheter 33 is slid onto stem 34 until the proximal end of the catheter engages flange 38, there being a snug fit between the catheter and the stem. In this system, the locking retainer shown generally at 42 comprises a retainer sleeve 44 and a locking ring 46 which are slightly different from those parts of system 10.

The sleeve 44 includes a tubular section 44a at its distal end having a longitudinal passage 43, flared at its distal end, for snugly receiving catheter 33. The sleeve also includes a pair of integral, collinear, hinged-together, mirror image, semicylindrical sections 44b and 44c, somewhat similar to those in sleeve 18 described above. The internal walls of sleeve sections 44b and 44c are provided with lengthwise passage segments 47 having registering semicylindrical recesses 48 adjacent the proximal end of the sleeve. These are arranged to receive flange 38 when the sleeve is slid along the catheter to the position shown in FIG. 4. Then, when sleeve section 44c is swung to its closed position shown in that figure, flange 38 is captured in recesses 48.

In the FIG. 4 system, the inner walls of passage segments 47 have opposed linear series of, e.g. three, semicircular bosses or ribs 52 distributed along the length of those passage segments. When sleeve section 44c is swung to its closed position, three circular bands or segments 33b of catheter 33 are compressed between stem 34 and those ribs 52. These compressive engagements help to inhibit sliding motion of the catheter on the stem due to tensile forces on the catheter. If such sliding motion does occur, the sleeve 44 tends to be pulled along with the catheter. However, since the sleeve is retained by flange 38, such movement is prevented and the catheter ultimately fails in tension.

Sleeve section 44c is maintained in its closed position by locking ring 46 which is slidable on the sleeve from its unlocking position on sleeve section 44a to its locking position shown in FIG. 4 wherein it encircles and captures sleeve sections 44b and 44c. Preferably, the ring is externally tapered as shown to facilitate gripping it.

In other respects, the FIG. 4 connection system has all of the advantages discussed above in connection with system 10.

It will be seen from the foregoing, then, that our catheter connection system establishes a reliable, releasible, fluid-tight and easily made joint or connection between the end of a catheter and a rigid tube, stem or other fluid pathway. The system's sleeve and locking ring are easy to manipulate when connecting and disconnecting the catheter from the tube, even if the surgeon's view is obstructed. Yet, the components of the system are relatively easy and inexpensive to make so that the providing of this secure connection does not materially increase the overall cost of the injection portal or other prosthesis incorporating the invention.

What is claimed as new and desired to be secured by Letters Patent of the United States is:

1. Connection apparatus comprising
   A. a relatively rigid elongated stem, said stem having a free end and means defining a radial enlargement on the exterior surface of the stem at a selected location along the stem;
   B. a flexible tube having a lumen for tightly receiving a lengthwise segment of said stem including said free end thereof; and
   C. retainer means, said retainer means including
      1. a sleeve having a tubular distal sleeve segment with a lengthwise passage for snugly receiving said tube at a location thereon adjacent to the free end of said stem, and a proximal sleeve segment integral with the distal segment for releasably clamping around said stem enlargement; and
      2. means for locking said proximal sleeve segment to clamp said stem enlargement.

2. The connection apparatus defined in claim 1 wherein the distal end of said distal sleeve segment passage is flared.

3. The connection apparatus defined in claim 1 wherein said tube receives said stem including the stem enlargment.

4. The connection apparatus defined in claim 1 wherein said tube receives the free end of said stem, but not the stem enlargement.

5. The connection apparatus defined in claim 1 wherein said proximal sleeve segment includes
   A. mating first and second clamping sections, said first section being an integral lengthwise extension of said distal sleeve segment and being shaped to extend around a first sector of said stem enlargement and said second section being shaped to extend around a second sector of said stem enlargement; and
   B. means for hinging together said first and second sections along corresponding lengthwise edges so that the second section can be swung between a closed position wherein said first and second sections clamp around said stem enlargement and an open position wherein said first and second section do not clamp around said stem enlargement.

6. The connection apparatus defined in claim 5 wherein said hinge means are constituted by a living hinge extending between said first and second sections.

7. The connection apparatus defined in claim 5 wherein
   A. said first and second sections are semicylinders which form a tubular extension of said distal sleeve segment when said second section is in its closed position; and
   B. the interior surfaces of said first and second sections have grooves which receive said stem enlargement when the second section is in its closed position.

8. The connection apparatus defined in claim 7 wherein said locking means comprise a ring encircling said sleeve and movable therealong between a first position wherein it tightly encircles the proximal sleeve segment and urges said second section to its closed position and a second position wherein the ring encircles said distal sleeve segment thereby permitting said second section to be swung to its open position.

9. The connection apparatus defined in claim 8 and further including means for inhibiting the movement of said locking ring from its said first position.

10. The connection apparatus defined in claim 1 wherein
    A. said stem enlargement is an axially symmetric, three dimensional barb with a tapered end located at said free end of said stem; and
    B. said distal sleeve segment passage is generally cylindrical with a cross-sectional area which is less than the maximum cross-sectional area of said barb.

11. The connection apparatus defined in claim 10 wherein said proximal sleeve segment comprises
    A. first and second mating, mirror-image, generally semicylindrical, hinged-together sections, said first section being an integral lengthwise extension of said distal sleeve segment and said second section being swingable between a closed position wherein said first and second sections form a tubular extension of said distal sleeve segment and an open position which exposes the interior surfaces of said first and second sections; and
    B. means defining a pair of semicircular, mating grooves in said interior surfaces of said first and second sections which are sized to snugly receive said stem enlargement and any catheter segment encircling said enlargement when said second section is swung to its closed position.

12. The connection apparatus defined in claim 11 wherein said locking means comprise a ring encircling said sleeve and movable therealong between a locking position wherein it tightly engages around said first and second sections and an unlocking position wherein it encircles said distal sleeve segment.

13. The connection apparatus defined in claim 1 wherein
    A. said stem is generally cylindrical;
    B. said stem enlargement is a circular flange spaced from said free end of said stem;
    C. said distal sleeve segment passage is generally cylindrical with a diameter that is slightly less than that of said free end of the stem.

14. The connection apparatus defined in claim 13 wherein said proximal sleeve segment comprises
    A. first and second mating, mirror-image, generally semicylindrical, hinged together sections, said first section being an integral lengthwise extension of said distal sleeve segment and said second section being swingable between a closed position wherein it forms with said first section a tubular extension of said distal sleeve segment and an open position which exposes the interior surface of said first and second sections;
    B. means defining a pair of mating semicircular grooves in said interior surfaces of said first and second sections which are sized to receive said stem enlargement when said second section is swung to its closed position; and
    C. means defining a lengthwise series of one or more pairs of mating semicircular ribs on said interior surfaces distal to said recesses, said ribs being sized to clamp around said stem and any flexible tube segment thereon when said second section swung to its closed position.

15. The connection apparatus defined in claim 14 wherein said locking means comprise a ring encircling said sleeve and movable therealong between a locking position wherein it tightly engages around said first and second sections and an unlocking position wherein it encircles said distal sleeve segment.

16. The connection apparatus defined in claim 14 wherein said locking means comprise a ring encircling said sleeve and movable therealong between a locking position wherein it tightly engages around said first and second sections and an unlocking position wherein it encircles said distal sleeve segment.

17. The connection apparatus defined in claim 16 and further including means for inhibiting the movement of said locking ring from its said first position.

18. Apparatus for connecting a relatively rigid elongated stem of the type having a free end and a radial enlargement on the exterior surface of the stem at a selected location along the stem to a flexible tube having a lumen tightly receiving a lengthwise segment of the stem including said free end thereof, said apparatus comprising
    A. a sleeve having a tubular distal sleeve segment with a lengthwise passage for snugly receiving the tube and a proximal sleeve segment integral with the distal segment for releasably clamping around the stem enlargement, said proximal sleeve segment comprising
       1. first and second mating, mirror-image, generally semicylindrical, hinged-together sections, said first section being an integral lengthwise extension of said distal sleeve segment and said second section being swingable between a closed position wherein said first and second sections form a tubular extension of said distal sleeve segment and an open position which exposes the interior surfaces of said first and second sections, and
2. means defining a pair of semicircular, mating grooves in said interior surfaces of said first and second sections, and B. means for locking said second section in said closed position.

19. The connection apparatus defined in claim 18 wherein said proximal sleeve segment further includes means defining a lengthwise series of one or more pairs of mating semicircular ribs on the segments of said interior surfaces distal to said recesses.

20. The apparatus defined in claim 18 wherein the distal end of said distal sleeve segment passage is flared.

* * * * *